United States Patent [19]

Chu

[11] Patent Number: 4,489,205

[45] Date of Patent: Dec. 18, 1984

[54] PREPARATION OF A GLUTARALDEHYDE PRECURSOR

[75] Inventor: Nan S. Chu, Hartsdale, N.Y.

[73] Assignee: Union Carbide Corporation, Danbury, Conn.

[21] Appl. No.: 507,976

[22] Filed: Jun. 28, 1983

Related U.S. Application Data

[63] Continuation-in-part of Ser. No. 266,102, May 21, 1981, abandoned.

[51] Int. Cl.$^3$ .................. C07D 309/10; C07C 47/12
[52] U.S. Cl. ................................. 549/417; 568/483
[58] Field of Search ...................... 549/417; 568/483

[56] References Cited

U.S. PATENT DOCUMENTS

| | | | |
|---|---|---|---|
| 2,546,018 | 3/1951 | Smith et al. | 568/483 |
| 2,564,649 | 8/1951 | Rogers | 260/345.9 R |
| 2,624,764 | 1/1953 | Emerson et al. | 260/345.9 R |
| 2,694,077 | 11/1954 | Stansbury et al. | |
| 2,931,837 | 4/1960 | Stanbury, Jr. et al. | 260/345.9 R |
| 4,244,876 | 1/1981 | Warner et al. | 260/345.9 R |

Primary Examiner—Nicky Chan
Attorney, Agent, or Firm—Henry H. Gibson

[57] ABSTRACT

Described herein is a process for the preparation of a novel essentially nonaqueous glutaraldehyde precursor which is capable of rapidly generating glutaraldehyde upon addition to water. The precursor is prepared by the hydration of 2-alkoxy-3, 4-dihydropyran in the presence of an acid catalyst.

10 Claims, No Drawings

PREPARATION OF A GLUTARALDEHYDE PRECURSOR

This invention is directed to a process for the preparation of a novel essentially nonaqueous glutaraldehyde precursor which is capable of rapidly generating glutaraldehyde upon addition to water. The precursor is prepared by the hydration of 2-alkoxy-3,4-dihydropyran in the presence of an acid catalyst.

Glutaraldehyde is widely used in many applications, such as leather tanning, embalming, photography and particularly as a microbiocide. Glutaraldehyde is generally prepared by the acid hydrolysis of 2-alkoxy-3,4-dihydropyran in a system containing a large excess of water. Without water, glutaraldehyde is generally not stable and polymerizes to a glass-mass on standing. Thus, it is always prepared as an aqueous solution. A commercial concentration generally contains from about 50 to about 98 percent water. However, even this aqueous glutaraldehyde solution is capable of polymerizing to an oligomer and/or to a polymer which precipitates from the aqueous solution on standing.

Further, glutaraldehyde undergoes an aldol condensation. The formation of these condensation products, as well as oligomers and/or polymers increases with, for example, increasing temperature, glutaraldehyde concentration, and pH.

The current processes for preparing glutaraldehyde have drawbacks. The formation of the condensation products and/or oligomers and polymers results in the loss of glutaraldehyde. Also, the use of 50 percent or more of water during the acid hydrolysis of the 2-alkoxy-3,4-dihydropyran decreases reactor capacity. Further, when the commercial 50 percent aqueous solution is shipped to warm climates, thermal stability of the solution becomes a serious problem. Also, in cold weather the agueous solution may freeze.

Thus, there is much interest in developing a nonaqueous precursor to glutaraldehyde capable of yielding glutaraldehyde upon its addition to water. Such a precursor could be stored or shipped in varying climates without the resulting problems now associated with an aqueous solution.

U.S. Pat. No. 4,244,876 (Warner et al.) describes the formation of a precursor to glutaraldehyde, i.e., 2,6-dimethoxytetrahydropyran. It is prepared by the addition of an alcohol to 2-methoxy-3,4-dihydropyran. However, the conditions under which the glutaraldehyde is produced from the 2,6-dimethoxytetrahydropyran are time consuming, since it requires several hours at low pH to generate a substantial amount of glutaraldehyde.

U.S. Pat. No. 2,546,018 (Smith et al.) discloses a process comprising heating a 2-alkoxy-3, 4-dihydropyran with water at a temperature and pressure, and for a time sufficient to produce an aqueous solution of glutaraldehyde and an alkanol by-product. The process conditions disclosed and all examples are directed towards the principal product of the reaction as glutaraldehyde. Thus, the problems associated with aqueous or nonaqueous glutaraldehyde still exist.

In the present invention a novel, essentially nonaqueous glutaraldehyde precursor has been discovered.

THE INVENTION

This invention is directed to a process for the preparation of a novel, essentially nonagueous glutaraldehyde precursor composition. The precursor is prepared by a process consisting essentially of hydrating 2-alkoxy-3,4-dihydropyran in the presence of an acid catalyst at a temperature of from about 30 to about 100° C. under such reaction conditions sufficient to produce principally said precursor, and wherein the molar ratio of water to 2-alkoxy-3, 4-dihydropyran is from about 1:1 to about 3:1. The hydration conditions to be used are such that materials containing appreciable and substantial carbonyl content are not produced, i.e., essentially no free glutaraldehyde is produced. A distillation step for product separation is therefore undesirable since it would result in the degradation of precursor producing glutaraldehyde product.

The glutaraldehyde precursor produced does not polymerize. Also, it has better thermal stability and a lower freezing point than a commercial 50 percent or greater glutaraldehyde solution. The glutaraldehyde precursor yields glutaraldehyde upon addition to water.

The reaction may be illustrated by the hydration of, for example, 2-methoxy-3, 4-dihydropyran:

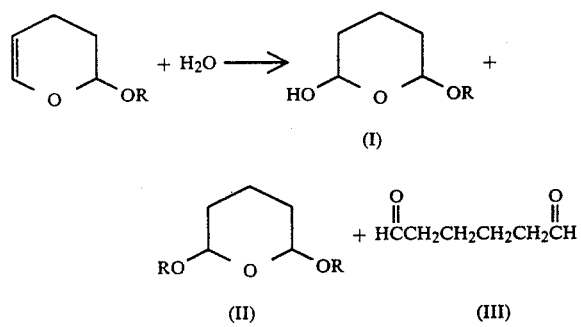

wherein R, the alkoxy group of the 2-alkoxy-3,4-dihydropyran, preferably contains from 1 to 3 carbon atoms.

The principal product is 2-hydroxyl-6-methoxytetrahydropyran (I) although trace amounts of 2,6-dimethoxytetrahydropyran (II), glutaraldehyde (III) and their isomers are formed.

The reaction is carried out in the presence of an acid catalyst. The acid catalyst may be an inorganic or an organic acid or an ion exchange resin. The acids which may be used herein include a strong mineral acid an acid-reacting salt, a material which will react under the conditions of the process to form, in situ, an acid-reacting material or a supported acid catalyst. These acid catalysts include phosphoric acid, hydrochloric acid, sulfuric acid, trifluoromethylsulfonic acid, para-toluenesulfonic acid, as well as supported acid catalysts, such as Amberlyst which is a supported arylsulfonic acid (sold by Rohm & Haas Company) and Nafion which is a supported fluorosulfonic acid (sold by E. I. duPont de Nemours Co.). When a liquid acid is used, the acid may be removed after hydration by neutralizing it with a base to form a salt and then removing the salt, as by filtration.

The reaction is carried out at a temperature of from about 30° to 100° C., and preferably from about 40° to about 90° C. The reaction temperature and time are dependent upon the type and amount of catalyst used in the reaction. The reaction temperature and conditions are sufficient to produce the glutaraldehyde precursor.

Such reaction conditions will vary depending upon the catalyst and reactants selected. More vigorous reaction conditions such as higher tempertures, refluxing and distillation, should be avoided to the extent glutaraldehyde precursor is lost, through the formation of undesired glutaraldehyde. The limits to such reaction conditions may be readily determined by those skilled in the art using reaction mixture evaluation during the reaction.

The reaction is generally carried out at atmospheric pressure, although subatmospheric and superatmospheric pressures may be used.

The molar ratio of water to 2-alkoxy-3, 4-dihydropyran in the reaction is from about 1:1 to about 3:1, and preferably from about 1:1 to about 2:1. The use of larger amounts of water offer no advantages since reactor capacity is reduced and the shelf-life of the reaction product is reduced.

Following hydration the glutaraldehyde precursor composition may be cooled to room temperature (about 25° C.) and isolated from the catalyst by, for example, filtration.

The reaction product may be used as such. It is added to water to produce glutaraldehyde. Increased yields of glutaraldehyde can be obtained by providing an acid during water addition. The water may contain optional ingredients such a colorants, thickeners, fragrances, and the like. However, water is the predominant material.

EXAMPLES

The following examples serve to give specific illustrations of the practice of this invention but they are not intended in any way to limit the scope of this invention.

EXAMPLE 1

A 250 ml 4-necked round bottom flask, fitted with a condenser, a mechanical stirrer, a thermometer and a nitrogen inlet was used as the reaction vessel. The flask was flushed with nitrogen and 114 g. of 2-methoxy-3,4-dihydropyran, 21.6 g. of distilled water and 13.2 g of Rexyn 101, a sulfonated polystyrene (supplied by Fisher Scientific Co.) were added. The catalyst resin was prewashed with distilled water to remove most of the water soluble acids which might be present. The resin contained 5 milliequivalents of acid per gram of dry resin. The reaction mixture was kept in a constant temperature bath of 50° C. The hydration was followed gas chromatographically (Hewlett-Packard Model 5710A) to completion by the disappearance of the 2-methoxy-3,4-dihydropyran peak. The reaction was carried out for about 2 to 2½ hours. The reaction was cooled to room temperature (about 25° C.) and the reaction product filtered. A slightly yellow liquid was obtained. The yield was about 98 percent.

EXAMPLES 2 TO 4

The procedure described in Example 1 was exactly repeated except that the molar ratio of water to 2-methoxy-3,4-dihydropyran was varied in Examples 2 to 4 as follows: 1.2/1.0; 2.0/1.0 and 5.6/1.0. After the reaction was complete, portions of the reaction products were stored in an oven set at a temperature of 60° C. for 27 days of thermal aging. 25 percent solutions of the aged samples in water were prepared and their UV absorbence (at 233 nm) were measured in a 0.1 mm silica cell (vs. air). (Beckman ACTA Model M VIII). The absorbences of the reaction product before and after thermal aging are listed in Table I. The 233 nm absorbence indicates the formation of undesirable aldol type condensation products.

TABLE I

| Example | Mole Ratio of $H_2O/MDP$[1] When Made | Unheated | After 27 days at 60° C. | % Increase |
|---|---|---|---|---|
| 2 | 1.2 | 0.751 | 1.001 | 33 |
| 3 | 2.0 | 0.454 | 0.650 | 43 |
| 4 | 5.6 | 0.347 | 1.414 | 307 |

[1]MDP = 2-methoxy-3,4-dihydropyran

The data in Table I show that as the ratio of water to 2-methoxy-3,4-dihydropyran increases the solutions are less thermally stable.

EXAMPLES 5 TO 7

These Examples demonstrate the rapid generation of glutaraldehyde when the reaction products produced by the hydration of 2-methoxy-3, 4-dihydropyran are added to water at room temperature (about 25° C.). The reaction products were prepared as described in Example 1 with the mole ratio of water to 2-methoxy-3,4-dihydropyran in Examples 5 to 7 as follows: 1.0/1.0; 1.5/1.0 and 2.0/1.0. Within five minutes after addition to water, gas chromatograph analyses was used to show the generation of the glutaraldehyde. These aqueous solutions were prepared to contain eguivalent amounts of 2-methoxy-3,4-dihydropyran.

TABLE II

| Examples | Concentration of solution of the hydration product (ppm)[1] | Mole Ratio of $H_2O/MDP$[2] when made | Glutaraldehyde found (ppm)[1] |
|---|---|---|---|
| 5 | 132 | 1.0/1.0 | 67.2 |
| 6 | 136 | 1.5/1.0 | 73.3 |
| 7 | 150 | 2.0/1.0 | 80.0 |

[1]ppm = parts per million
[2]MDP = 2-methoxy-3,4-dihydropyran

EXAMPLES 8 TO 10

These Examples demonstrate the heat stability of the reaction product produced by the hydration of 2-methoxy-3,4-dihydropyran prepared as in Example 1. The mole ratio of water to 2-methoxy-3,4-dihydropyran in Examples 8 to 10 was as follows: 1.2/1.0; 1.5/1.0 and 2.0/1.0. The reaction products were thermally aged for the time periods and at the temperatures shown in Table III. After thermally aging, the reaction products were added to water to reflect an equivalent initial pyran concentration. Gas chromatograph analysis was used to show the concentration of glutaraldehyde. The untreated sample was also analyzed. Control A is a 50 percent glutaraldehyde solution. The results are shown in Table III.

TABLE III

| | | Glutaraldehyde (ppm) | | |
|---|---|---|---|---|
| Example | Mole Ratio of $H_2O/MDP$[1] When Made | Untreated | After 9 days at 60° C. | After 27 days at 60° C. |
| 8 | 1.2/1.0 | 74.2 | 73.3 | 73.5 |
| 9 | 1.5/1.0 | 75.1 | 72.2 | 76.0 |
| 10 | 2.0/1.0 | 79.4 | 80.0 | 81.0 |
| Control A | 50% glutaraldehyde solution | 97.5 | 92.0 | 86.6 |

[1]MDP = 2-methoxy-3,4-dihydropyran

The data in Table III show that the reaction product of this invention is more thermally stable than the 50 percent aqueous glutaraldehyde solution.

EXAMPLES 11 TO 14

These Examples demonstrate that the rapid generation of glutaraldehyde from the 2-hydroxy-6-methoxytetrahydropyran reaction product make this product a very effective microbiocide. The products were prepared by the procedure described in Example 1. The mole ratio of water to 2-methoxy-3,4-dihydropyran in Examples 11 to 14 was as follows: 1.0/1.0; 1.2/1.0; 1.5/1.0 and 2.0/1.0. The concentration of reaction products required to kill all the *Staphylococcus aureus* ($10^7$ colony forming units/milliliter) present with 2 hours contact time using a solution having a pH of 7 are shown in Table IV.

TABLE IV

| Examples | Mole Ratio of $H_2O/MDP^2$ when made | Concentration of reaction product required (ppm$^2$ as made) |
|---|---|---|
| 11 | 1.0 | 66 |
| 12 | 1.2 | 68 |
| 13 | 1.5 | 70 |
| 14 | 2.0 | 75 |

$^1$MDP = 2-methoxy-3,4-dihydropyran
$^2$ppm = parts per million

EXAMPLE 15

The procedure described in Example 1 was exactly repeated except that the amounts of materials used were as follows: 28.5 g of 2-methoxy-3,4-dihydropyran, 5.4 g of distilled water and 6.6 g of catalyst. Also, the reaction was carried out at a temperature of 35° C. instead of 50° C. The reaction was complete in about 2 hours.

EXAMPLE 16

The procedure in Example 1 was exactly repeated except that the amounts of materials used were as follows: 28.5 g of 2-methoxy-3, 4-dihydropyran and 4.5 g of distilled water. Also 1.0 g of Nafion-511, H (0.95 milliequivalents per gram, supplied by E. I. duPont de Nemours & Co.) was used instead of the Rexyn 101 catalyst. The reaction was complete in about 40 minutes.

EXAMPLE 17

The procedure in Example 1 was exactly repeated except that the amounts of materials used were as follows: 28.5 g of methoxy-3,4-dihydropyran and 5.4 g of distilled water. Also, 0.5 g of an 85 percent phosphoric acid solution was used as the catalyst instead of Rexyn 101. The reaction was carried out at a temperature of 90° C. instead of 50° C. The reaction was complete in about 90 minutes. The reaction product was cooled to room temperature (about 25° C.) and adjusted to a pH of 7 with 0.36 g of sodium bicarbonate. The reaction product was filtered to remove a small amount of precipitate.

EXAMPLE 18

The procedure of Example 17 was exactly repeated except that 1.0 g of the phosphoric acid solution was used. Also, the reaction was carried out at a temperature of 65° C. The reaction was complete in about 2 to 2½ hours. The reaction product was cooled to room temperature (about 25° C.) and adjusted to a pH of 7 with 0.72 g of sodium bicarbonate. The reaction product was filtered to remove a small amount of precipitate.

What is claimed is:

1. A process for producing a glutaraldehyde precursor composition substantially free of glutaraldehyde which consists essentially of hydrating 2-alkoxy-3,4-dihydropyran in contact with an acid catalyst at a temperature of from about 30° to about 100° C. without refluxing and under such reaction conditions sufficient to produce essentially said precursor, wherein the molar ratio of water to 2-alkoxy-3, 4-dihydropyran is from about 1:1 to about 3:1 and wherein the alkoxy group contains from 1 to 3 carbon atoms.

2. The process of claim 1 wherein the 2-alkoxy-3,4-dihydropyran is 2-methoxy-3, 4-dihydropyran.

3. The process of claim 1 wherein following said hydration the glutaraldehyde precursor composition is cooled to about 25° C. and isolated.

4. The process of claim 1 wherein following said hydration the glutaraldehyude precursor is isolated without distillation.

5. A process for producing an agueous solution of glutaraldehyde which comprises adding the glutaraldehyde precursor composition produced by the process of claim 1 to water.

6. The glutaraldehyde precursor composition produced by the process of claim 1 comprising principally 2-hydroxy-6-methoxytetrahydropyran.

7. A process for producing an agueous solution of glutaraldehyde which comprises adding 2-hydroxy-6-methoxytetrahydropyran to water.

8. 2-Hydroxy-6-methoxytetrahydropyran.

9. An essentially nonaqueous composition comprising principally 2-hydroxy-6-methoxytetrahydropyran and a trace amount of 2,6-dimethoxytetrahydropyran.

10. The essentially nonaqueous composition of claim 9 comprising principally 2-hydroxy-6-methoxytetrahydropyran, with trace amounts of 2,6-dimethoxytetrahydropyran and glutaraldehyde.

* * * * *